(12) United States Patent
Altmejd et al.

(10) Patent No.: US 11,759,120 B2
(45) Date of Patent: Sep. 19, 2023

(54) PLETHYSMOGRAPH

(71) Applicant: SCIREQ Scientific Respiratory Equipment Inc., Montreal (CA)

(72) Inventors: Simon Altmejd, Montreal (CA); Annette Robichaud, Ville Mont-Royal (CA); Ilan Benjamin Urovitch, Cote-St-Luc (CA); Camilo Guevara Garzon, Montreal (CA)

(73) Assignee: SCIREQ SCIENTIFIC RESPIRATORY EQUIPMENT INC., Montreal (CA)

( * ) Notice: Subject to any disclaimer, the term of this patent is extended or adjusted under 35 U.S.C. 154(b) by 757 days.

(21) Appl. No.: 16/592,036

(22) Filed: Oct. 3, 2019

(65) Prior Publication Data

US 2020/0107752 A1   Apr. 9, 2020

(30) Foreign Application Priority Data

Oct. 5, 2018   (CA) ................................. CA 3020011

(51) Int. Cl.
*A61B 5/08*   (2006.01)
*G02B 5/20*   (2006.01)
*A01K 1/03*   (2006.01)

(52) U.S. Cl.
CPC .......... *A61B 5/0806* (2013.01); *A01K 1/031* (2013.01); *G02B 5/20* (2013.01); *A61B 2503/40* (2013.01); *A61B 2503/42* (2013.01)

(58) Field of Classification Search
CPC ................................ A61B 5/0806; G02B 5/20
See application file for complete search history.

(56) References Cited

U.S. PATENT DOCUMENTS

| | | | |
|---|---|---|---|
| 5,379,777 A | 1/1995 | Lomask | |
| 2006/0278218 A1 | 12/2006 | Hoffman | |
| 2007/0179394 A1* | 8/2007 | Sheehan | A61B 5/0806 600/529 |
| 2010/0217358 A1 | 8/2010 | Hebert | |
| 2012/0213895 A1* | 8/2012 | Rasmussen | B65D 1/0207 426/106 |

FOREIGN PATENT DOCUMENTS

EP   1638462 B1   12/2009

OTHER PUBLICATIONS

"Tech Spec Filters." Edmund Optics Brochure, Edmund Optics, Jan. 19, 2017, www.edmundoptics.com/ViewDocument/TECHSPEC_Filters_17_en.pdf. (Year: 2017).*

* cited by examiner

*Primary Examiner* — Tse W Chen
*Assistant Examiner* — Clarissa Cuevas
(74) *Attorney, Agent, or Firm* — Volpe Koenig

(57) ABSTRACT

The present disclosure concerns a plethysmograph. The plethysmograph comprises a housing defining a test cavity configured to enclose a test subject. The plethysmograph further comprises an optical filter providing a spectrally restricted optical access to the test cavity from an exterior of the housing, the optical filter being configured to at least partially transmit light in a transmission band ranging from about 560 nm to about 750 nm; and to at least partially block light in a blocking band ranging from about 380 nm to about 560 nm.

15 Claims, 12 Drawing Sheets

PLETHYSMOGRAPH

PRIOR APPLICATION

The present application claims priority from Canadian patent application CA 3 020 011, filed on Oct. 5, 2018, and entitled "IMPROVED PLETHYSMOGRAPH", the disclosure of which being hereby incorporated by reference in its entirety.

TECHNICAL FIELD

The technical field relates to plethysmographs used for measuring changes in air volume, and in particular, to plethysmographs used to assess lung properties of small animals.

BACKGROUND

Plethysmographs are commonly used in studies to evaluate aspects of the respiratory function of conscious subjects, such as small animals. Plethysmographs can either be configured for the subject to freely move inside a test cavity (whole body plethysmograph—WBP) or they can be configured to isolate the subject mouth and nose from its thoracic cage between two separate test cavities (double chamber plethysmograph—DCP).

Whole body plethysmographs usually comprise a housing defining the test cavity configured to enclose the test subject. The housing is usually made of clear plexiglass for the test subject to be observable from the outside of the test cavity during a recording session. However, the test subject might become very anxious when placed in the test cavity and it is known that the induced stress can have significant impacts on the scientific outcomes.

Moreover, a typical test cavity consists of a closed volume with a restrictive opening to the outside atmosphere called pneumotach, and a tube connected to a differential pressure sensor. The pneumotach usually comprises an air opening on which a resistive screen has been placed. As the subject is breathing inside the test cavity, the act of inhaling and exhaling creates pressure variations that can be recorded by the differential pressure sensor. But because the pneumotach provides an air opening to the outside atmosphere, any outside change of pressure entering the test cavity through the pneumotach is likely to also be measured by the differential pressure sensor and added to the signal, causing an unwanted phenomenon called background noise.

In view of the above, there is a need for an improved plethysmograph which would be able to overcome or at least minimize some of the above-discussed prior art concerns.

BRIEF SUMMARY

It is therefore an aim of the present invention to address the above-mentioned issues.

According to a general aspect, there is provided a plethysmograph comprising a housing defining a test cavity configured to enclose a test subject, and an optical filter providing a spectrally restricted optical access to the test cavity from an exterior of the housing. The optical filter is configured to at least partially transmit light in a transmission band ranging from about 560 nm to about 750 nm and to at least partially block light in a blocking band ranging from about 380 nm to about 560 nm.

According to another general aspect, there is provided a plethysmograph comprising a housing defining a test cavity configured to enclose a test subject, and an optical filter to provide a spectrally restricted optical access to the test cavity from an exterior of the housing. The optical filter is configured to at least partially transmit light in a transmission band encompassing at least one of the red, orange and yellow portions of the electromagnetic spectrum and to at least partially block light in a blocking band at least partially encompassing at least one of the green, blue and violet portions of the electromagnetic spectrum.

According to another general aspect, there is provided a whole-body plethysmograph comprising a housing forming a test chamber and a reference chamber. The test chamber defines a test cavity configured to enclose a test subject and comprises a test pneumotach having a test pneumotach body in which a test airflow opening is formed, for the test cavity to be in fluid communication with the outside of the housing, the test airflow opening defining a test airflow surface having a geometrical center. The reference chamber defines a reference cavity and comprises a reference pneumotach having a reference pneumotach body in which a reference airflow opening is formed, for the reference cavity to be in fluid communication with the outside of the housing, the reference airflow opening defining a reference airflow surface having a geometrical center. The whole-body plethysmograph further comprises an optical filter providing a spectrally restricted optical access to the test cavity from an exterior of the housing, wherein the optical filter is configured to at least partially transmit light in a transmission band ranging from about 560 nm to about 750 nm; and to at least partially block light in a blocking band ranging from about 380 nm to about 560 nm. The geometrical centers of the test airflow surface and the reference airflow surface substantially correspond to each other. One of the test airflow opening and the reference airflow opening has a substantially cylindrical shape and the other one of the test airflow opening and the reference airflow opening has a substantially annular shape.

According to another general aspect, there is provided a plethysmograph comprising a housing forming a test chamber and a reference chamber. The test chamber defines a test cavity configured to enclose a test subject and comprises a test pneumotach having a test pneumotach body in which a test airflow opening is formed, for the test cavity to be in fluid communication with the outside of the housing. The reference chamber defines a reference cavity and comprises a reference pneumotach having a reference pneumotach body in which a reference airflow opening is formed, for the reference cavity to be in fluid communication with the outside of the housing. One of the test pneumotach body and the reference pneumotach body at least partially extends in the other one of the test pneumotach body and the reference pneumotach body.

According to another general aspect, there is provided a plethysmograph comprising a housing forming a test chamber and a reference chamber. The test chamber defines a test cavity configured to enclose a test subject and comprises a test pneumotach having a test pneumotach body in which a test airflow opening is formed, for the test cavity to be in fluid communication with the outside of the housing. The reference chamber defines a reference cavity and comprises a reference pneumotach having a reference pneumotach body in which a reference airflow opening is formed, for the reference cavity to be in fluid communication with the outside of the housing. One of the test airflow opening and the reference airflow opening at least partially surrounds the other one of the test airflow opening and the reference airflow opening.

According to another general aspect, there is provided a plethysmograph comprising a housing forming a test chamber defining a test cavity configured to enclose a test subject. The test cavity is in fluid communication with the outside of the housing via a test airflow opening. The housing further forms a reference chamber defining a reference cavity in fluid communication with the outside of the housing via a reference airflow opening. One of the test airflow opening and the reference airflow opening at least partially surrounds the other of the test airflow opening and the reference airflow opening.

According to another general aspect, there is provided a plethysmograph comprising a housing forming a test chamber and a reference chamber. The test chamber defines a test cavity configured to enclose a test subject and comprises a test pneumotach having a test pneumotach body in which a test airflow opening is formed, for the test cavity to be in fluid communication with the outside of the housing. The test airflow opening defines a test airflow surface having a geometrical center. The reference chamber defines a reference cavity and comprises a reference pneumotach having a reference pneumotach body in which a reference airflow opening is formed, for the reference cavity to be in fluid communication with the outside of the housing. The reference airflow opening defines a reference airflow surface having a geometrical center. One of the test airflow surface and the reference airflow surface further comprises the geometrical center of the other one of the test airflow surface and the reference airflow surface.

According to another general aspect, there is provided a plethysmograph comprising a housing defining a test cavity configured to enclose a test subject and comprising a test pneumotach. The test pneumotach has a test pneumotach body in which a test airflow opening is formed, for the test cavity to be in fluid communication with the outside of the housing and a test resistive screen at least partially covering the test airflow opening configured to restrict the flow of air into and out of the test chamber. The test resistive screen comprises at least one layer of a non-conductive substrate.

According to another general aspect, there is provided a plethysmograph comprising a housing defining a reference cavity comprising a reference pneumotach. The reference pneumotach has a reference pneumotach body in which a reference airflow opening is formed, for the reference cavity to be in fluid communication with the outside of the housing and a reference resistive screen at least partially covering the reference airflow opening configured to restrict the flow of air into and out of the reference chamber. The reference resistive screen comprises at least one layer of a non-conductive substrate.

Other possible aspect(s), object(s), embodiment(s), variant(s) and/or advantage(s) of the present invention, all being preferred and/or optional, are briefly summarized hereinbelow.

DETAILED DESCRIPTION

Figure 1:
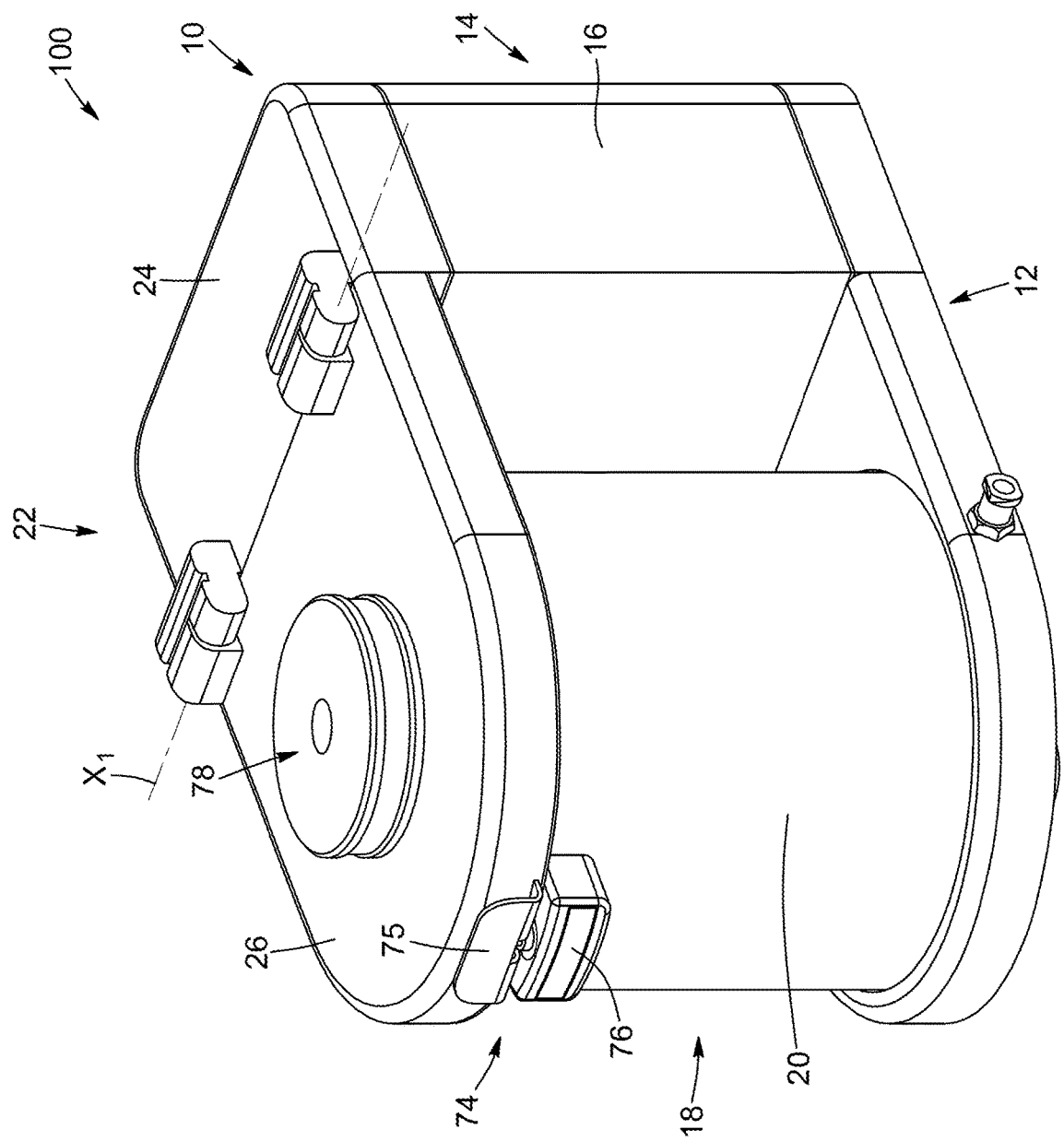
FIG. 1 is a front perspective view of a plethysmograph having a housing forming a test chamber and a reference chamber, the test chamber being configured in a closed configuration, the plethysmograph further comprising a test pneumotach and a reference pneumotach.

In the following description, the same numerical references refer to similar elements. Furthermore, for the sake of simplicity and clarity, namely so as to not unduly burden the figures with several reference numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

Moreover, it will be appreciated that positional descriptions such as "above", "below", "forward", "rearward", "left", "right" and the like should, unless otherwise indicated, be taken in the context of the figures only and should not be considered limiting. Moreover, the figures are meant to be illustrative of certain characteristics of the plethysmograph and are not necessarily to scale.

To provide a more concise description, some of the quantitative expressions given herein may be qualified with the term "about". It is understood that whether the term "about" is used explicitly or not, every quantity given herein is meant to refer to an actual given value, and it is also meant to refer to the approximation to such given value that would reasonably be inferred based on the ordinary skill in the art, including approximations due to the experimental and/or measurement conditions for such given value.

In the following description, an embodiment is an example or implementation. The various appearances of "one embodiment", "an embodiment" or "some embodiments" do not necessarily all refer to the same embodiments. Although various features may be described in the context of a single embodiment, the features may also be provided separately or in any suitable combination. Conversely, although the invention may be described herein in the context of separate embodiments for clarity, it may also be implemented in a single embodiment. Reference in the specification to "some embodiments", "an embodiment", "one embodiment" or "other embodiments" means that a particular feature, structure, or characteristic described in connection with the embodiments is included in at least some embodiments, but not necessarily all embodiments.

It is to be understood that the phraseology and terminology employed herein are not to be construed as limiting and are for descriptive purpose only. The principles and uses of the teachings of the present disclosure may be better understood with reference to the accompanying description, figures and examples. It is to be understood that the details set forth herein do not construe a limitation to an application of the disclosure.

Furthermore, it is to be understood that the disclosure can be carried out or practiced in various ways and that the disclosure can be implemented in embodiments other than the ones outlined in the description above. It is to be understood that the terms "including", "comprising", and grammatical variants thereof do not preclude the addition of one or more components, features, steps, or integers or groups thereof and that the terms are to be construed as specifying components, features, steps or integers. If the specification or claims refer to "an additional" element, that does not preclude there being more than one of the additional element. It is to be understood that where the claims or specification refer to "a" or "an" element, such reference is not be construed that there is only one of that element. It is to be understood that where the specification states that a component, feature, structure, or characteristic "may", "might", "can" or "could" be included, that particular component, feature, structure, or characteristic is not required to be included.

The descriptions, examples, methods and materials presented in the claims and the specification are not to be construed as limiting but rather as illustrative only. Meanings of technical and scientific terms used herein are to be commonly understood as by one of ordinary skill in the art to which the invention belongs, unless otherwise defined. It will be appreciated that the methods described herein may be performed in the described order, or in any suitable order.

Referring now to the drawings, there is shown a plethysmograph 100 that is configured to assess lung properties of a test subject, such as a small animal, for instance but without being limitative a mouse or a rat.

General Structure of the Plethysmograph

In the embodiment shown, the plethysmograph 100 comprises a housing 10 comprising a base (or bottom wall) 12 extending substantially horizontally and configured to support the plethysmograph 100 on a supporting surface.

The housing 10 further comprises a lateral portion 14 extending substantially vertically, the lateral portion 14 forming a reference chamber 16, the function of which will be further described.

The housing 10 comprises a substantially cylindrical body 18, extending substantially vertically and forming a test chamber 20 defining a test cavity 21 configured to enclose the test subject.

The housing 10 further comprises an upper wall 22 comprising a fixed wall portion 24 configured to extend substantially horizontally above the lateral portion 14, and a pivotable cover portion 26, pivotably mounted to the fixed wall portion 24, and configured to extend substantially horizontally above the cylindrical body 18. In the embodiment shown, the pivotable cover portion 26 is pivotably mounted to the fixed wall portion 24 about a pivot axis X1. In the embodiment shown, the pivot axis X1 extends substantially horizontally.

Figure 2:
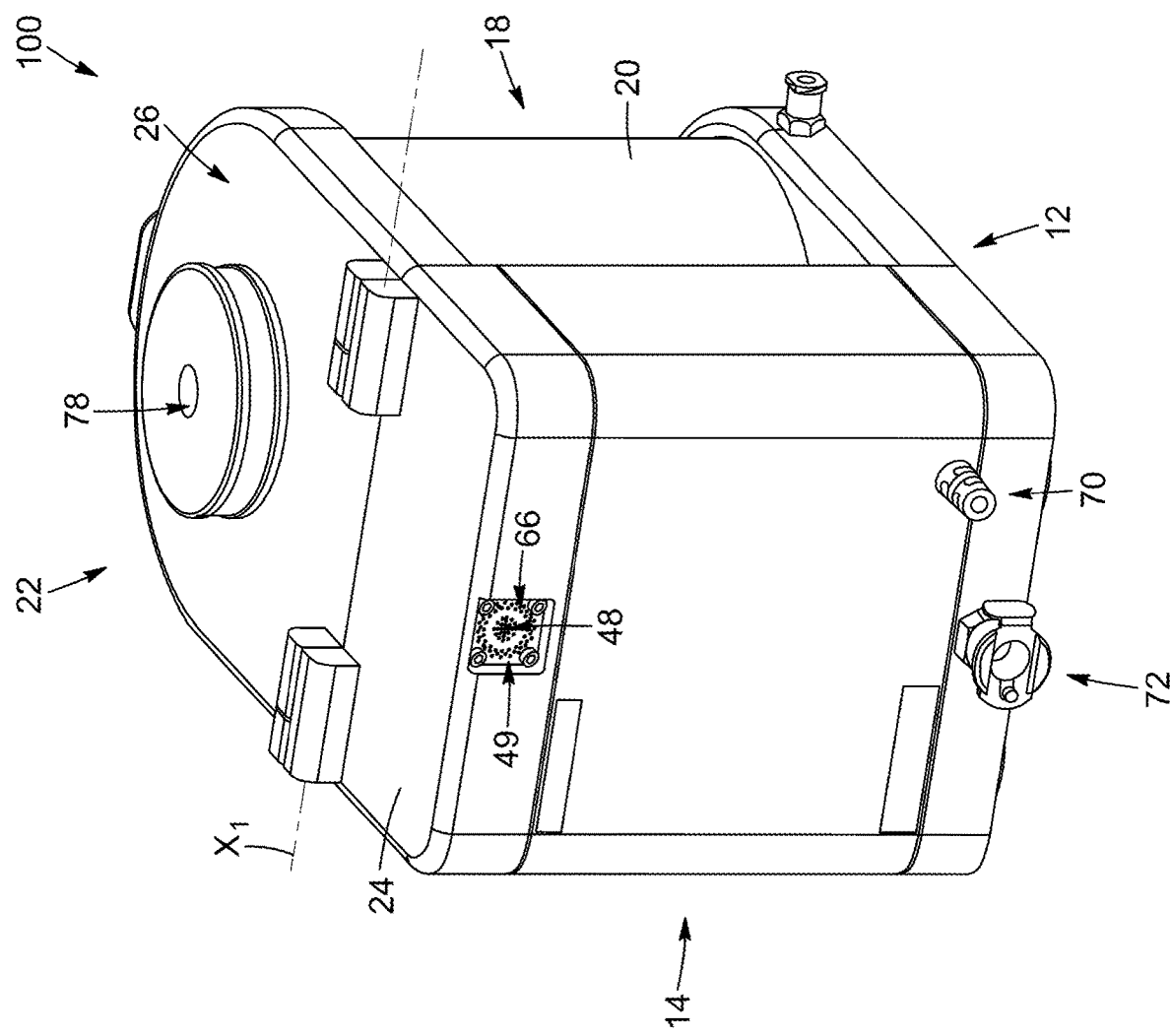
FIG. 2 is a rear perspective view of the plethysmograph of FIG. 1.
Figure 3:
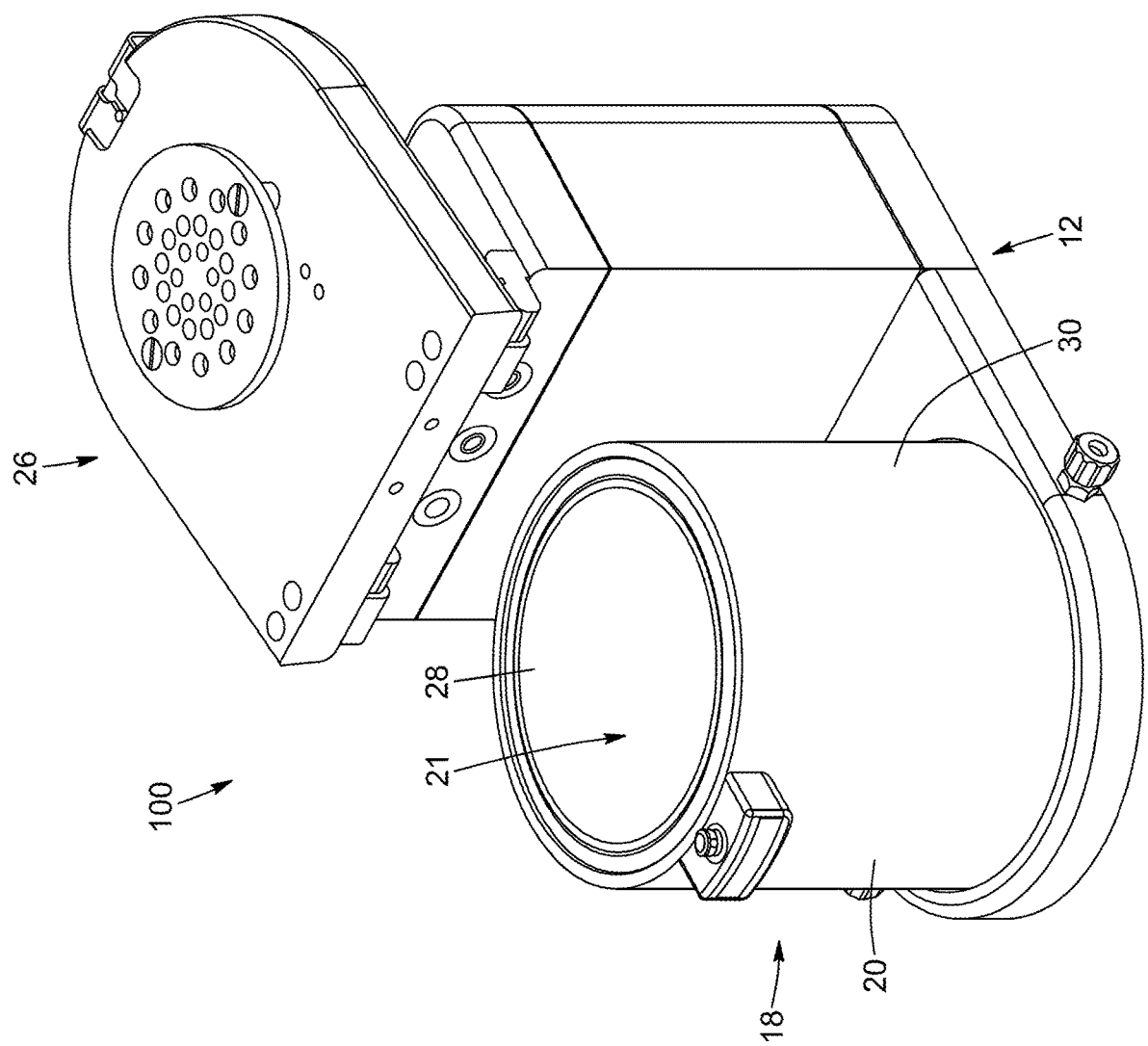
FIG. 3 is a front perspective view of the plethysmograph of FIG. 1, the test chamber being configured in an open configuration.
Figure 4:
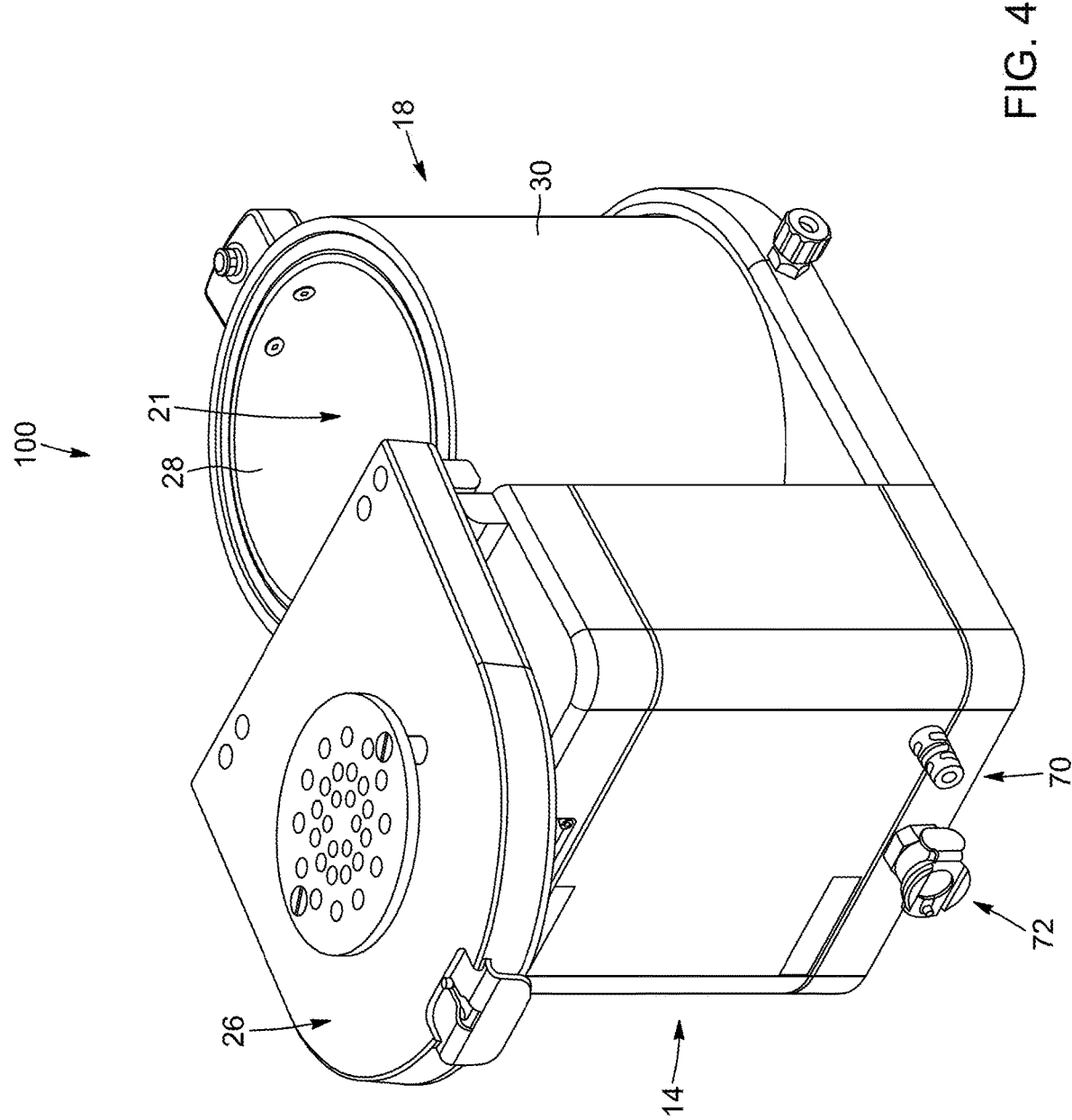
FIG. 4 is a rear perspective view of the plethysmograph of FIG. 3.
Figure 5:
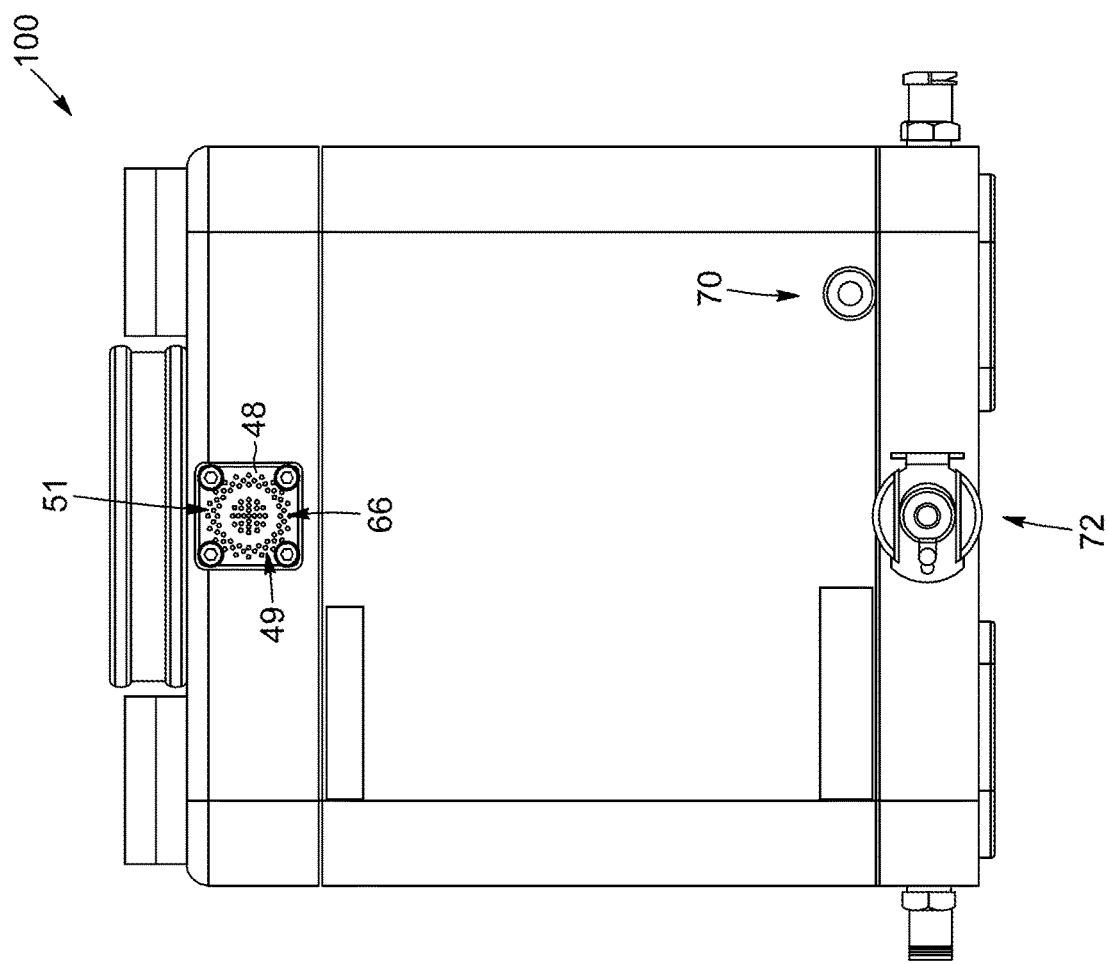
FIG. 5 is a rear elevational view of the plethysmograph of FIG. 1.
Figure 6:
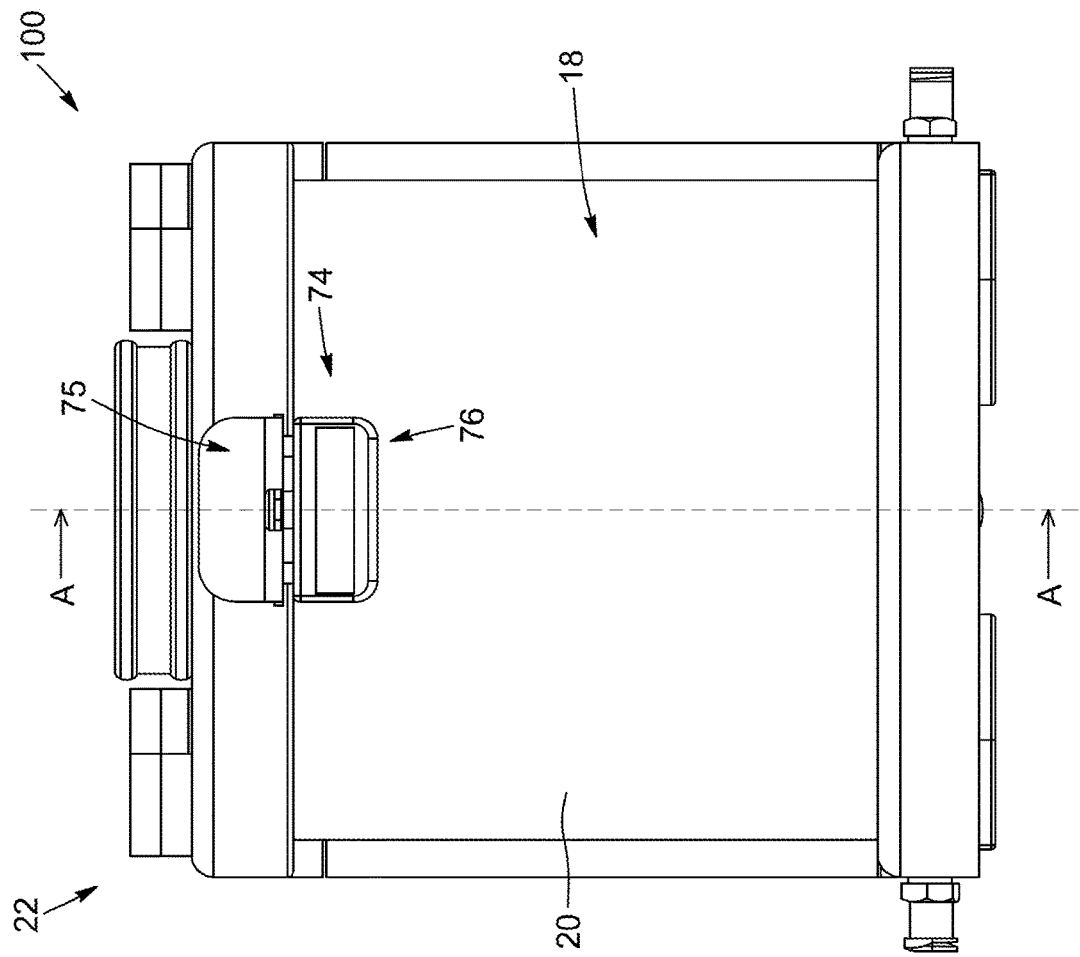
FIG. 6 is a front elevational view of the plethysmograph of FIG. 1.
Figure 7:
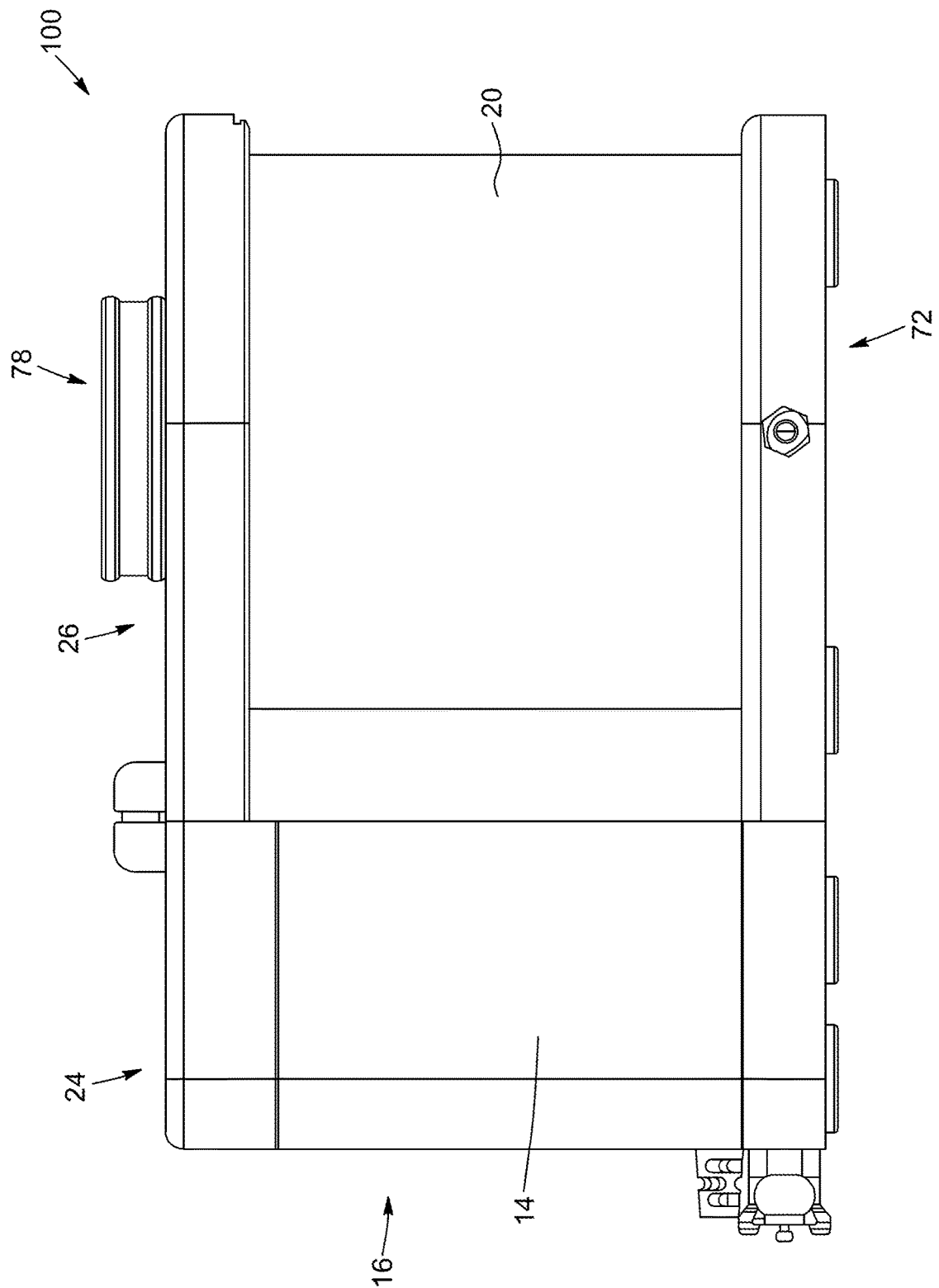
FIG. 7 is a left elevational view of the plethysmograph of FIG. 1.
Figure 8:
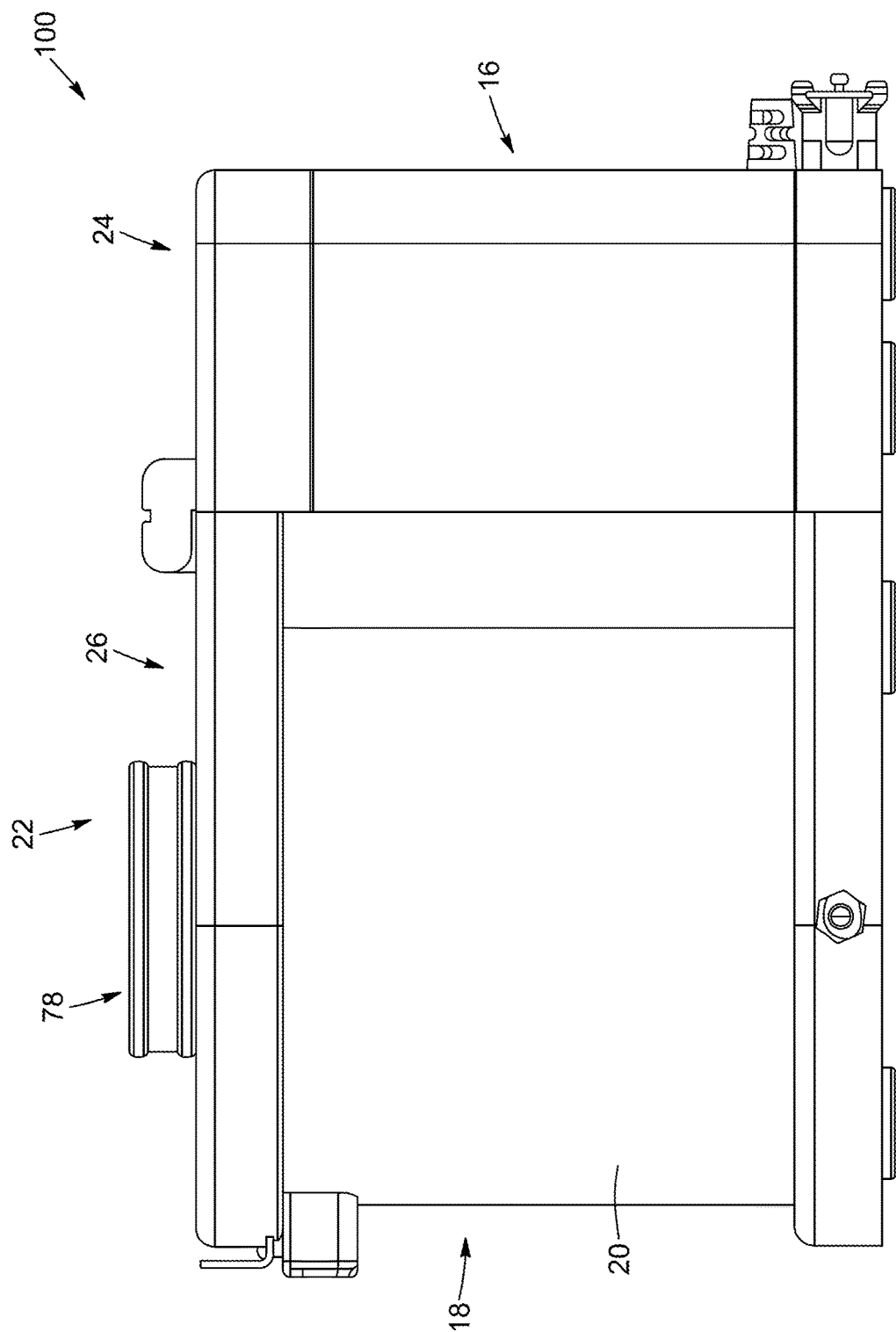
FIG. 8 is a right elevational view of the plethysmograph of FIG. 1.

It is thus understood that the test chamber 20 is either configured in a closed configuration, as represented in FIGS. 1 and 2, in which the pivotable cover portion 26 substantially covers the cylindrical body 18 so as to at least substantially close the test cavity 21, or configured in an open configuration, as represented in FIGS. 3 and 4, for the test subject to be introduced into or removed from the test cavity 21 of the test chamber 20.

It is appreciated that the shape, the dimensions and the configuration of the housing 10 and its different components can vary from the embodiment shown.

The plethysmograph 100 further comprises a bias flow port 72 configured to be connected to a vacuum flow source to provide the test subject with fresh air. In the embodiment shown, but without being limitative, the bias flow port 72 also extends from the lateral portion 14 of the housing 10.

Test Chamber

In the embodiment shown, the test chamber 20 of the plethysmograph 100 is configured for the test subject to freely move inside the test chamber 20. In other words, in the embodiment shown, the plethysmograph 100 is a whole-body plethysmograph. The present disclosure is however not limited to a whole-body plethysmograph and could alternatively be a double-chamber plethysmograph.

The housing 10 further comprises an optical filter providing a spectrally restricted optical access to the test cavity 21 from an exterior of the housing 10. In the embodiment shown, the cylindrical body 18 of the housing 10 comprises the optical filter. In the embodiment shown, the optical filter substantially covers an entirety of the surfaces surrounding the test chamber 20.

In the embodiment shown, the test subject is a small animal, such as a mouse or a rat. Being prey animals, mice and rats can become very anxious in a new environment, especially when they feel exposed with no possibility to hide. It is well-known that the induced stress can have significant impacts on the scientific outcomes. Since the measurements are made while the test subject is conscious, measures directed at reducing outcome variability aim to reduce the test subject anxiety level.

Because mice and rats are also nocturnal animals, they tend to be calmer in dark environments. Calmer subjects lead to shorter acclimation time and more regular breathing patterns, which makes the data more consistent, easier to interpret and more reproducible.

Moreover, plethysmographs are typically placed in clear see-through chambers inside an illuminated lab, allowing researchers to observe the test subject inside the test chamber 20 while potentially causing a lot of anxiety on the test subject.

It is further known that mice and rats only have a dichromatic vision, perceiving only blue and green wavelengths.

In the present description, the terms "light" and "optical", and any variants and derivatives thereof, are intended to refer to electromagnetic radiation in any appropriate region of the electromagnetic spectrum, and they are not limited to visible light. The visible spectrum is the portion of the electromagnetic spectrum that is visible to the human eye. Electromagnetic radiation in this range of wavelengths is called visible light or simply light.

Visible light is commonly divided into various bands corresponding to various colors. More particularly, visible light is commonly divided into violet, corresponding to wavelengths from about 380 nm to about 450 nm, blue, corresponding to wavelengths from about 450 nm to about 495 nm, green, corresponding to wavelengths from about 495 nm to about 570 nm, yellow, corresponding to wavelengths from about 570 nm to about 590 nm, orange, corresponding to wavelengths from about 590 nm to about 620 nm, and red, corresponding to wavelengths from about 620 nm to about 750 nm. Ultraviolet (UV) is electromagnetic radiation with a wavelength commonly extending from about 10 nm to about 400 nm.

In the embodiment shown, the optical filter is thus configured to at least partially transmit (or permit passage of) light in a transmission band ranging from about 560 nm to about 750 nm, and to at least partially block (or prevent passage of) light in a blocking band ranging from about 380 nm to about 560 nm.

In an embodiment, the optical filter is configured to transmit at least about 15% light in a transmission band ranging from about 560 nm to about 750 nm. In another embodiment, the optical filter is configured to transmit at least about 25% light in a transmission band ranging from about 560 nm to about 750 nm. In another embodiment, the optical filter is configured to transmit at least about 40% light in a transmission band ranging from about 560 nm to about 750 nm. In another embodiment, the optical filter is configured to transmit at least about 55% light in a transmission band ranging from about 560 nm to about 750 nm. In another embodiment, the optical filter is configured to transmit at least about 70% light in a transmission band ranging from about 560 nm to about 750 nm. In another embodiment, the optical filter is configured to transmit at least about 85% light in a transmission band ranging from about 560 nm to about 750 nm. In another embodiment, the optical filter is configured to transmit at least about 95% light in a transmission band ranging from about 560 nm to about 750 nm. In yet another embodiment, the optical filter is configured to transmit substantially entirely light in a transmission band ranging from about 560 nm to about 750 nm.

In an embodiment, the optical filter is configured to block at least about 15% light in a blocking band ranging from about 380 nm to about 560 nm. In another embodiment, the optical filter is configured to block at least about 25% light in a blocking band ranging from about 380 nm to about 560 nm. In another embodiment, the optical filter is configured to block at least about 40% light in a blocking band ranging from about 380 nm to about 560 nm. In another embodiment, the optical filter is configured to block at least about 55% light in a blocking band ranging from about 380 nm to about 560 nm. In another embodiment, the optical filter is configured to block at least about 70% light in a blocking band ranging from about 380 nm to about 560 nm. In another embodiment, the optical filter is configured to block at least about 85% light in a blocking band ranging from about 380 nm to about 560 nm. In another embodiment, the optical filter is configured to block at least about 95% light in a blocking band ranging from about 380 nm to about 560 nm. In yet another embodiment, the optical filter is configured to block substantially entirely light in a blocking band ranging from about 380 nm to about 560 nm.

In another embodiment, the optical filter is configured to at least partially transmit (or permit passage of) light in a transmission band ranging from about 600 nm to about 750 nm, and to at least partially block (or prevent passage of) light in a blocking band ranging from about 380 nm to about 600 nm. In another embodiment, the optical filter is configured to at least partially transmit (or permit passage of) light in a transmission band ranging from about 620 nm to about 750 nm, and to at least partially block (or prevent passage of) light in a blocking band ranging from about 380 nm to about 620 nm.

In the embodiment shown, the optical filter is configured to at least partially transmit (or permit passage of) light in a transmission band encompassing at least one of the red, orange and yellow portions of the electromagnetic spectrum and to at least partially block (or prevent passage of) light in a blocking band at least partially encompassing at least one of the green, blue and violet portions of the electromagnetic spectrum.

In the embodiment shown, the optical filter is configured to at least partially block light in a blocking band at least partially encompassing at least one of the green, blue and ultraviolet portions of the electromagnetic spectrum.

In an embodiment, the optical filter is configured to transmit at least about 15% light in a transmission band encompassing at least one of the red, orange and yellow portions of the electromagnetic spectrum. In another embodiment, the optical filter is configured to transmit at least about 25% light in a transmission band encompassing at least one of the red, orange and yellow portions of the electromagnetic spectrum. In another embodiment, the optical filter is configured to transmit at least about 40% light in a transmission band encompassing at least one of the red, orange and yellow portions of the electromagnetic spectrum. In another embodiment, the optical filter is configured to transmit at least about 55% light in a transmission band encompassing at least one of the red, orange and yellow portions of the electromagnetic spectrum. In another embodiment, the optical filter is configured to transmit at least about 70% light in a transmission band encompassing at least one of the red, orange and yellow portions of the electromagnetic spectrum. In another embodiment, the optical filter is configured to transmit at least about 85% light in a transmission band encompassing at least one of the red, orange and yellow portions of the electromagnetic spectrum. In another embodiment, the optical filter is configured to transmit at least about 95% light in a transmission band encompassing at least one of the red, orange and yellow portions of the electromagnetic spectrum. In yet another embodiment, the optical filter is configured to transmit substantially entirely light in a transmission band encompassing at least one of the red, orange and yellow portions of the electromagnetic spectrum.

In an embodiment, the optical filter is configured to block at least about 15% light in a blocking band at least partially encompassing at least one of the green, blue and violet portions of the electromagnetic spectrum. In another embodiment, the optical filter is configured to block at least about 25% light in a blocking band at least partially encompassing at least one of the green, blue and violet portions of the electromagnetic spectrum. In another embodiment, the optical filter is configured to block at least about 40% light in a blocking band at least partially encompassing at least one of the green, blue and violet portions of the electromagnetic spectrum. In another embodiment, the optical filter is configured to block at least about 55% light in a blocking band at least partially encompassing at least one of the green, blue and violet portions of the electromagnetic spectrum. In another embodiment, the optical filter is configured to block at least about 70% light in a blocking band at least partially encompassing at least one of the green, blue and violet portions of the electromagnetic spectrum. In another embodiment, the optical filter is configured to block at least about 85% light in a blocking band at least partially encompassing at least one of the green, blue and violet portions of the electromagnetic spectrum. In another embodiment, the optical filter is configured to block at least about 95% light in a blocking band at least partially encompassing at least one of the green, blue and violet portions of the electromagnetic spectrum. In yet another embodiment, the optical filter is configured to block substantially entirely light in a blocking band at least partially encompassing at least one of the green, blue and violet portions of the electromagnetic spectrum.

In the embodiment shown, the cylindrical body 18 of the housing 10 is at least partially made of a substantially transparent material, such as glass, plexiglass, or any other convenient material.

The cylindrical body 18 comprises an inner surface 28, facing the test cavity 21 of the test chamber 20, and an opposed outer surface 30. In the embodiment shown, the optical filter comprises a tinted film at least partially covering at least one of the inner surface 28 and the outer surface 30 of the cylindrical body 18.

In another embodiment, the cylindrical body 18 of the housing 10 is at least partially made of a transparent colored material. For instance, but without being limitative, the material at least partially forming the cylindrical body 18 is colored by a coloring oil or a coloring paint.

In the embodiment shown, the cylindrical body 18 is at least partially made of a substantially orange material. The cylindrical body 18 is thus configured to at least partially transmit light in a transmission band encompassing the red portion of the electromagnetic spectrum, while at least partially blocking light in a transmission band encompassing the green and blue portions of the electromagnetic spectrum.

The housing 10 is thus configured to allow observation of the test subject during the recording session, while limiting the stress of the test subject. In other words, the optical filter is configured to create an environment substantially dark for the test subject placed in the test cavity 21, in comparison with a plethysmograph having no optical filter, while allowing researchers to look inside the test cavity 21 of the plethysmograph 100.

It has thus been observed that the coefficient of variation of breathing frequencies of test subjects placed in the test chamber 21 of the plethysmograph 100 according to the present disclosure is smaller than the coefficient of variation of breathing frequencies of test subjects placed in a plethysmograph having no optical filter. In some embodiments, the coefficient of variation for test subjects placed in the test chamber 21 in accordance with the present disclosure can represent a reduction of the coefficient of variation for test subjects placed in a plethysmograph without an optical filter. In other words, the optical filter allows a more constant breathing frequency of the test subject, thus making the results of the plethysmograph 100 more reproducible in comparison with prior art plethysmographs.

Moreover, it has been observed that the duration of the acclimation sessions, prior to the measures of the aspects of the respiratory function of the test subject in the plethysmograph according to the present disclosure, can be significantly reduced in comparison with prior art plethysmographs having no optical filter.

It is appreciated that the shape, the configuration, and the location of the optical filter can vary from the embodiment shown.

In particular, the optical filter might either be distinct from the housing 10, or be a part of the housing 10. In particular, it could be conceived an external housing (not represented) dimensioned to at least partially surround the housing 10, the external housing comprising the optical filter, for the external housing to provide a spectrally restricted optical access to the test cavity from an exterior of the housing 10.

Test Pneumotach

The test chamber 20 comprises a test pneumotach 32 having a test pneumotach body 34 in which a test airflow opening 36 is formed, for the test cavity 21 to be in fluid communication with the outside of the housing 10. In other words, the test cavity 21 is in fluid communication with the outside of the housing 10 via the test airflow opening 36.

The test chamber 20 further comprises a tube (not represented) connected to a test sensor port of a differential pressure sensor 60. In the embodiment shown, but without being limitative, the differential pressure sensor 60 is arranged below the reference chamber 50.

In the embodiment shown, the test pneumotach body 34 is formed integral with the upper wall 22 of the housing 10, and more particularly integral with the fixed wall portion 24 of the upper wall 22, so that the test airflow opening 36 opens in the upper wall 22. More particularly, in the embodiment shown, the test airflow opening 36 opens in a lateral side 23 of the upper wall 22.

Figure 11:
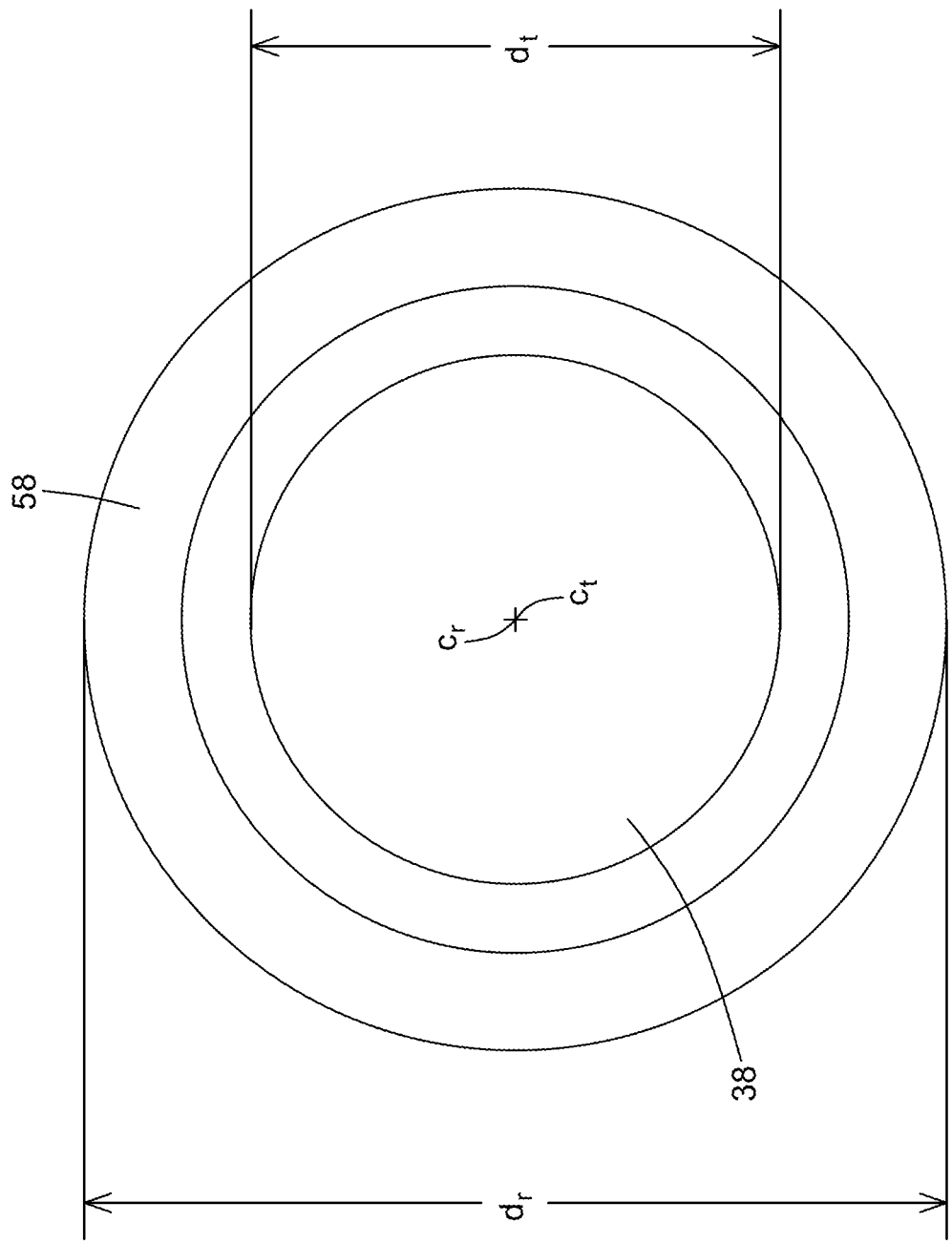
FIG. 11 is a cross-sectional view of the test pneumotach and the reference pneumotach of the plethysmograph of FIG. 1.

In the embodiment shown, the test airflow opening 36 has a substantially cylindrical shape and defines a substantially horizontal axis Xt. As represented in FIG. 11, the test airflow opening 36 defines a test airflow surface 38 having a geometrical center Ct. In the embodiment shown, the test airflow surface 38 has a substantially circular shape defining a diameter dt. In an embodiment, the test airflow surface 38 has a surface area comprised between about 10 mm$^2$ and about 60 mm$^2$. In another embodiment, the surface area of the test airflow surface 38 is comprised between about 20 mm$^2$ and about 50 mm$^2$. In yet another embodiment, the surface area of the test airflow surface 38 is about 32 mm$^2$. In yet some other embodiments, the surface area of the test airflow surface 38 is about 12 mm$^2$.

It is appreciated that the shape, the configuration, and the location of the test pneumotach 32, and in particular the shape, the configuration and the location of the test airflow opening 36, can vary from the embodiment shown.

In the embodiment shown, a test airflow line 40 extends between the test airflow opening 36 and the test chamber 20 for the test chamber 20 to be in fluid communication with the outside of the housing 10 via the test airflow opening 36. In the embodiment shown, the test airflow line 40 extends substantially horizontally when the test chamber 20 is configured in the closed configuration and comprises a proximal portion 42 extending in the pivotable cover portion 26, and a distal portion 44 extending in the fixed wall portion 24. The proximal portion 42 of the test airflow line 40 opens, in the embodiment shown, in an upper portion of the test cavity 21. In the embodiment shown, the test airflow line 40 extends substantially along the horizontal axis Xt of the test airflow opening 36.

It is appreciated that the shape, the configuration, and the location of the test airflow line 40 can vary from the embodiment shown. It could also be conceived a plethysmograph 100 having a test chamber 20 in which the test airflow opening 36 would be directly formed.

The test pneumotach 32 further comprises a test resistive screen 46 extending in the test airflow opening 36 and configured to restrict the flow of air into and out of the test chamber 21, and thereby creating a pressure drop in the test chamber 21 when the test chamber 21 is connected to the vacuum source through the bias flow port 72.

In the embodiment shown, the test resistive screen 46 comprises a resistive plate 48 extending substantially vertically, in which a plurality of apertures are formed for the test airflow opening 36 to be in fluid communication with the outside of the housing 10. In the embodiment shown, the resistive plate has a central portion forming the test resistive screen 46. In the embodiment shown, a screen receiving opening 51 is formed in the upper wall 22 that is configured to receive the plate 48, but the resistive screen 46 could alternatively be secured directly to an outer surface of the housing 10. The plate 48 is secured, for instance via a plurality of fasteners 47 (four, in the embodiment shown) to a portion of the upper wall 22. In other words, the resistive plate 48 is secured to the housing 10. In the embodiment shown, but without being limitative, the resistive plate 48 is at least partially made of glass fiber, steel or aluminum. In the embodiment shown, the apertures have a diameter comprised between about 10 and about 50 thousandth of inch. In another embodiment, the apertures formed in the test resistive screen 46 have a diameter comprised between about 15 and about 40 thousandth of inch. In another embodiment, the apertures formed in the test resistive screen 46 have a diameter comprised between about 25 and about 35 thousandth of inch. In another embodiment, the apertures formed in the test resistive screen 46 have a diameter of the order of 30 thousandth of inch. In yet another embodiment, some apertures have a diameter of about 15 thousandth of inch, while some other apertures have a diameter of about 20 thousandth of inch, while yet some other apertures have a diameter of about 25 thousandth of inch, while yet some other apertures have a diameter of about 30 thousandth of inch.

In the embodiment shown, the test resistive screen 46 comprises at least a layer of a non-conductive substrate of a printed circuit board. In another embodiment, the test resistive screen 46 comprises one or more layers of copper laminated onto and/or between one or more layers of a non-conductive substrate. In the embodiment shown, the test resistive screen 46 is at least partially made of a printed circuit board. For instance, the test resistive screen 46 comprises at least two layers of a non-conductive substrate, said at least one layer of copper being laminated between the at least two layers of a non-conductive substrate.

In the embodiment shown, the resistive plate 48 has a substantially square shape, and the screen receiving opening 51 has a substantially parallelepipedal shape. It is appreciated that the shape, the configuration, and the location of the resistive plate 48 forming the test resistive screen 46 can vary from the embodiment shown.

Reference Chamber

As mentioned above, since the test pneumotach 32 provides an air opening to the outside atmosphere, any outside change of pressure entering the test chamber 20 through the test pneumotach 32 is likely to also be measured by the differential pressure sensor 60 and added to the signal, causing an unwanted phenomenon called background noise.

The above-mentioned reference chamber 16, arranged next to the test chamber 20, is configured to attenuate the background noise. Similarly to the test chamber 20, the reference chamber 16 defines a reference cavity 50 and comprises a reference pneumotach 52 and a tube connected to a reference sensor port 62 of the differential pressure sensor 60. This configuration allows any outside pressure disturbance to be recorded simultaneously by the test sensor port and the reference sensor port 62 of the differential pressure sensor 60, while the pressure variation caused by the test subject breathing in the test chamber 20 is only recorded by one. When the signals coming from the test sensor port and the reference sensor port 62 of the differential pressure sensor 60 are subtracted, any outside perturbation influence is cancelled out, theoretically removing any background noise. The subtraction of the pressure signals from the test and reference chamber is called noise cancellation. An example of a plethysmograph comprising a test chamber and a reference chamber is disclosed in EP 1 638 462.

Reference Pneumotach

The reference pneumotach 52 has a reference pneumotach body 54 in which a reference airflow opening 56 is formed, for the reference cavity 50 to be in fluid communication with the outside of the housing 10. In other words, the reference cavity 50 is in fluid communication with the outside of the housing 10 via the reference airflow opening 56.

In the embodiment shown, the reference pneumotach body 54 is formed integral with the upper wall 22 of the housing 10, and more particularly integral with the fixed wall portion 24 of the upper wall 22, so that the reference airflow opening 56 opens in the upper wall 22. More particularly, in the embodiment shown, the reference airflow opening 56 opens in the lateral side 23 of the upper wall 22.

In the embodiment shown, the reference airflow opening 56 has a substantially annular shape and defines a substantially horizontal axis Xr. As represented in FIG. 11, the reference airflow opening 56 defines a reference airflow surface 58 having a geometrical center Cr. In the embodiment shown, the reference airflow surface 58 defines a diameter dr. In an embodiment, the reference airflow surface 58 has a surface area comprised between about 40 mm$^2$ and about 80 mm$^2$. In another embodiment, the surface area of the reference airflow surface 58 is comprised between about 50 mm$^2$ and about 70 mm$^2$. In yet another embodiment, the surface area of the reference airflow surface 58 is about 65 mm$^2$.

It is appreciated that the shape, the configuration, and the location of the reference pneumotach 52, and more particularly, the shape, the configuration and the location of the reference airflow opening 56, can vary from the embodiment shown.

In the embodiment shown, the reference airflow opening 56 opens in an upper portion of the reference cavity 50.

The reference pneumotach 52 further comprises a reference resistive screen 66 extending in the reference airflow opening 56 and configured to restrict the flow of air into and out of the reference chamber 16.

In the embodiment shown, the reference resistive screen 66 is formed by a peripheral portion 49 of the above-described resistive plate 48 extending substantially vertically. A plurality of apertures are formed in the peripheral portion 49 of the plate 48 for the reference airflow opening 56 to be in fluid communication with the outside of the housing 10. In the embodiment shown, the apertures have a diameter comprised between about 10 and about 25 thousandth of inch. In another embodiment, the apertures have a diameter comprised between about 15 and about 20 thousandth of inch. In yet another embodiment, the apertures have a diameter of the order of 17 thousandth of inch In yet another embodiment, some apertures have a diameter of about 15 thousandth of inch, while some other apertures have a diameter of about 20 thousandth of inch, while yet some other apertures have a diameter of about 25 thousandth of inch, while yet some other apertures have a diameter of about 17 thousandth of inch.

In the embodiment shown, the reference resistive screen 66 comprises at least a layer of a non-conductive substrate of a printed circuit board. In another embodiment, the reference resistive screen 66 comprises one or more layers of copper laminated onto and/or between one or more layers of a non-conductive substrate. In the embodiment shown, the reference resistive screen 66 is at least partially made of a printed circuit board. For instance, the reference resistive screen 66 comprises at least two layers of a non-conductive substrate, the at least one layer of copper being laminated between the at least two layers of a non-conductive substrate.

In the embodiment shown, the test resistive screen 46 and the reference resistive screen 66 both comprise at least one layer of a non-conductive substrate of a printed circuit board. In another embodiment, the test resistive screen 46 and the reference resistive screen 66 comprise one or more layers of copper laminated onto and/or between one or more layers of a non-conductive substrate. In the embodiment shown, the test resistive screen 46 and the reference resistive screen 66 are both at least partially made of a printed circuit board. In the embodiment shown, the resistive plate 48 forming both the test resistive screen 46 and the reference resistive screen 66 is at least partially made of a printed circuit board.

It is appreciated that the shape, the configuration, and the location of the reference resistive screen 66 can vary from the embodiment shown. In particular, it could be conceived a plethysmograph in which the reference resistive screen 66 and the test resistive screen 46 would be formed of two distinct elements, possibly but not necessarily secured to each other.

Relative Arrangement of the Test Pneumotach and the Reference Pneumotach

Figure 9:
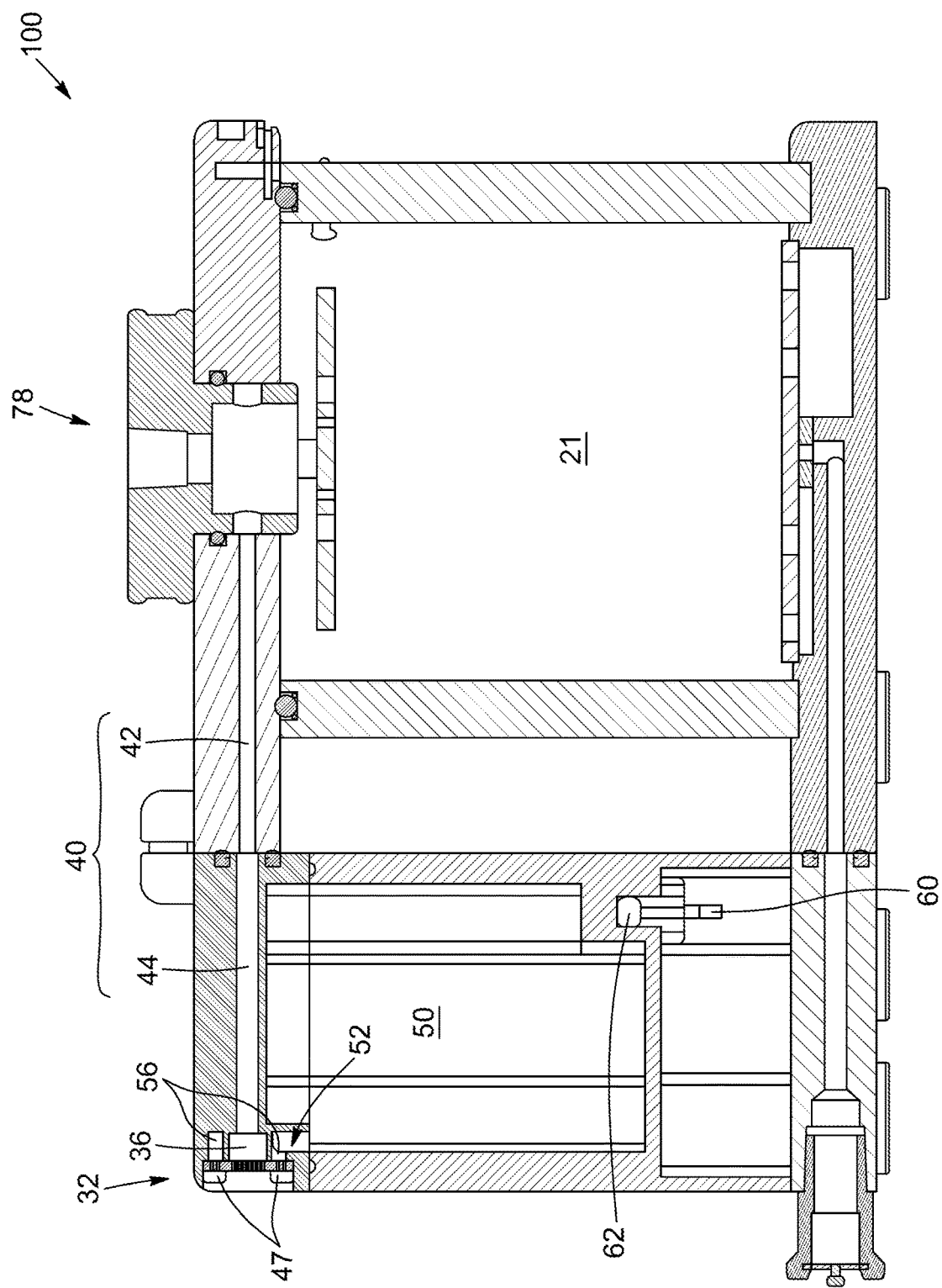
FIG. 9 is a sectional view taken along cross-section lines A-A of FIG. 6.
Figure 10:
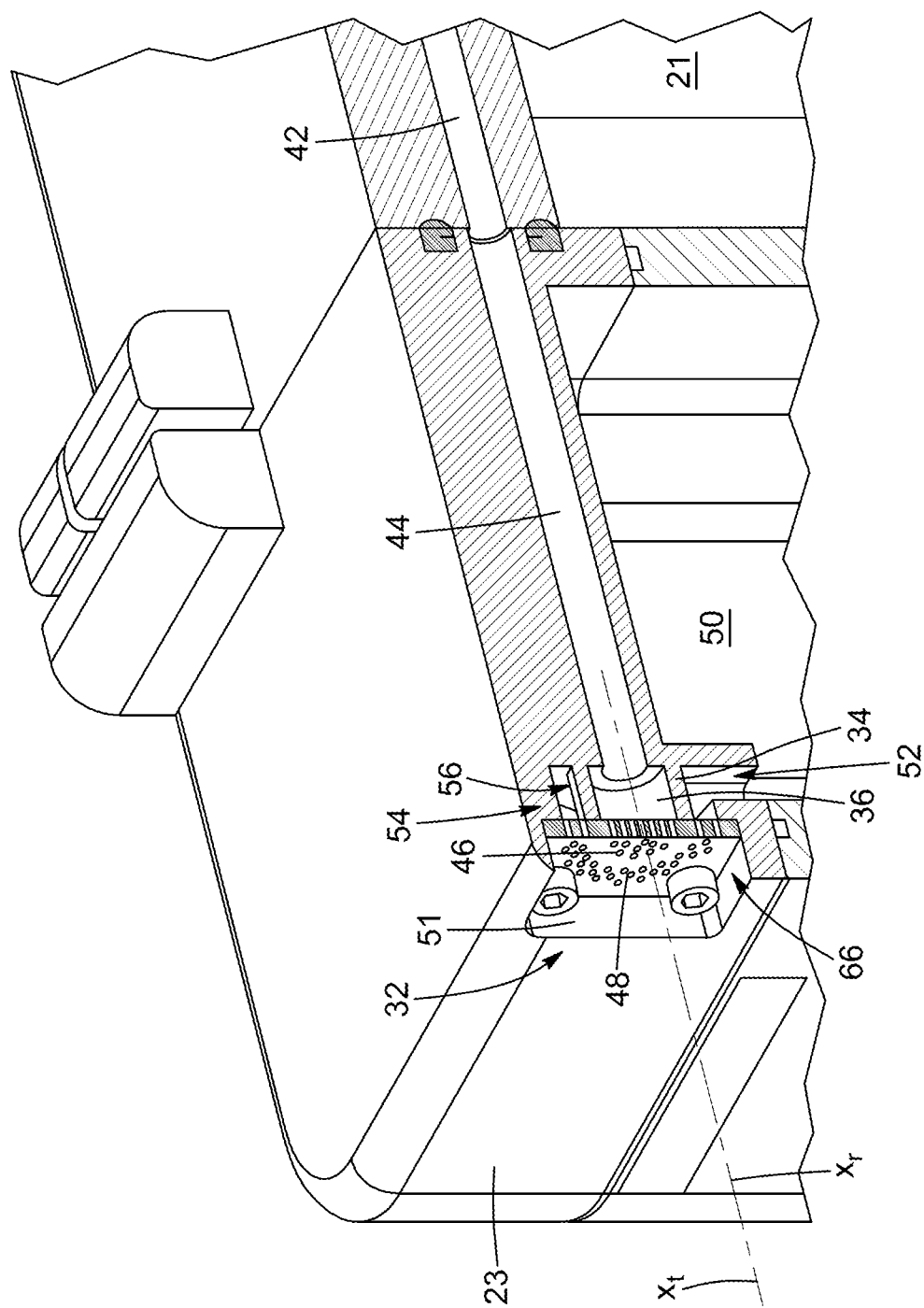
FIG. 10 is a top perspective enlarged view of the plethysmograph of FIG. 9.

As represented in particular in FIGS. 9 and 10, the plethysmograph 10 according to the present disclosure is configured so that the test pneumotach body 34 at least partially extends in the reference pneumotach body 54. In other words, in the embodiment shown, the reference airflow opening 56 at least partially surrounds the test airflow opening 36.

Figure 12:
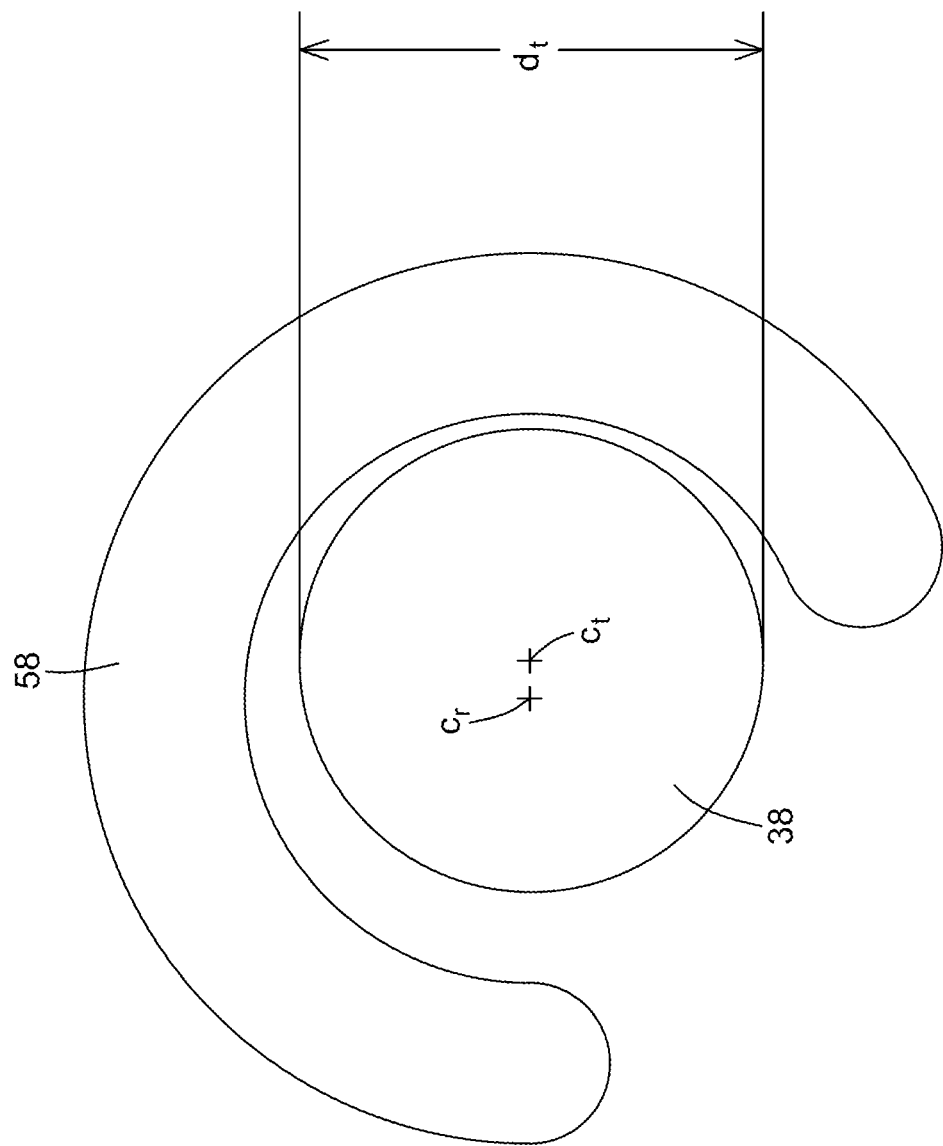
FIG. 12 is a cross-sectional view of the test pneumotach and the reference pneumotach of a plethysmograph in accordance with another embodiment.

In an embodiment, the reference airflow opening 56 surrounds at least about 15% of the test airflow opening 36. In another embodiment, the reference airflow opening 56 surrounds at least about 30% of the test airflow opening 36. In another embodiment, the reference airflow opening 56 surrounds at least about 45% of the test airflow opening 36. In another embodiment, the reference airflow opening 56 surrounds at least about 60% of the test airflow opening 36. In another embodiment, as represented in FIG. 12, the reference airflow opening 56 surrounds at least about 75% of the test airflow opening 36. In another embodiment, the reference airflow opening 56 surrounds at least about 90% of the test airflow opening 36. In yet another embodiment, as represented in FIG. 11, the reference airflow opening 56 surrounds substantially entirely the test airflow opening 36.

In the embodiment shown, the test airflow surface 38 comprises the geometrical center Cr of the reference airflow surface 58.

In an embodiment, the distance between the geometrical center Cr of the reference airflow surface 58 and the geometrical center Ct of the test airflow surface 38 is smaller than a predetermined distance. In another embodiment, the distance between the geometrical center Cr of the reference airflow surface 58 and the geometrical center Ct of the test airflow surface 38 is smaller than about 50% of the diameter dt of the test airflow surface 38. In another embodiment, the distance between the geometrical center Cr of the reference airflow surface 58 and the geometrical center Ct of the test airflow surface 38 is smaller than about 30% of the diameter dt of the test airflow surface 38. In another embodiment, the distance between the geometrical center Cr of the reference airflow surface 58 and the geometrical center Ct of the test airflow surface 38 is smaller than about 10% of the diameter dt of the test airflow surface 38. In yet another embodiment, the geometrical center Cr of the reference airflow surface 58 substantially corresponds to the geometrical center Ct of the test airflow surface 38. In other words, in another embodiment, the test airflow opening 36 and the reference airflow opening 56 are substantially concentric. In this embodiment, the axes Xr and Xt of the reference pneumotach body 54 and the test pneumotach body 34 are substantially coincident with each other.

In an embodiment, the diameter dt of the test airflow opening 36 represents at least about 10% of the diameter dr of the reference airflow opening 56. In another embodiment, the diameter dt of the test airflow opening 36 represents at least about 30% of the diameter dr of the reference airflow opening 56. In another embodiment, the diameter dt of the test airflow opening 36 represents at least about 50% of the diameter dr of the reference airflow opening 56. In another embodiment, the diameter dt of the test airflow opening 36 represents at least about 70% of the diameter dr of the reference airflow opening 56. In yet another embodiment, the diameter dt of the test airflow opening 36 represents at least about 80% of the diameter dr of the reference airflow opening 56.

It has been observed that noise cancellation performance increases when the distance between the test pneumotach 32 and the reference pneumotach 52 is decreased. In particular, it has been observed that the noise cancellation performance is substantially increased, in comparison with prior art plethysmographs, for perturbation having an amplitude greater than a predetermined threshold. In some embodiments, the noise cancellation performance is substantially increased for perturbation having an amplitude greater than about 0.005 L/min. In some other embodiments, the noise cancellation performance is substantially increased for perturbation having an amplitude greater than about 0.008 L/min.

It has further been observed that noise cancellation performance increases when a reference ratio between the resistance of the reference resistive screen 66 and a volume of the reference cavity 50 is substantially similar to a test ratio between the resistance of the test resistive screen 46 and a volume of the test cavity 21. In an embodiment, the volume of the reference cavity 50 is comprised between about 0.1 L and about 1 L, whereas the volume of the test cavity 21 is comprised between about 0.1 L and about 2 L. In another embodiment, the volume of the reference cavity 50 is comprised between about 0.3 L and about 0.5 L, whereas the volume of the test cavity 21 is comprised between about 0.4 L and about 0.6 L. In another embodiment, the volume of the reference cavity 50 is about about 0.4 L, whereas the volume of the test cavity 21 is about 0.5 L.

The resistance of the reference resistive screen 66 being a function of the surface of the reference resistive screen 66 and of the material in which the reference resistive screen 66 is formed, and the resistance of the test resistive screen 46 being a function of the surface of the test resistive screen 46 and of the material in which the test resistive screen 46 is formed, it is understood that the number and dimensions of the apertures formed in the portions of the resistive plate 48 facing the test airflow opening 36 and the reference airflow opening 56 should be adjusted for the above-mentioned reference ratio and test ratio to be as close to each other as possible.

It is appreciated that the shape, the configuration, and the location of the test pneumotach 32 and the reference pneumotach 52 can vary from the embodiment shown. In particular, the present disclosure is not limited to a configuration in which the reference airflow opening 56 at least partially surrounds the test airflow opening 36. A plethysmograph in which the reference airflow opening 56 would be at least partially surrounded by the test airflow opening 36 could for instance also be conceived.

Additional Technical Features

As represented in particular in FIGS. 1 to 10, the plethysmograph 100 further comprises a connector 70 configured to connect the differential pressure sensor 60 to a data acquisition system (for instance to a computer), in order to receive the data relative to the lung properties of the test subject. In the embodiment shown, but without being limitative, the connector 70 extends from the lateral portion 14 of the housing 10.

The plethysmograph 100 further comprises an injection opening 78 configured to inject a gas or a nebulization compound inside the test cavity 21. In the embodiment shown, the injection opening 78 is formed in the pivotable cover portion 26.

The plethysmograph 100 further comprises a closing assembly 74 configured to tightly close the test chamber 20 when configured in the closed configuration. In the embodiment shown, the closing assembly 74 comprises a first closing component 75 mounted to the pivotable cover portion 26, and a second closing component 76 mounted to the cylindrical body 18.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind. The scope of the invention is therefore intended to be limited by the scope of the appended claims. Of course, and as can be easily understood by a person skilled in the art, the scope of the claims should not be limited by the possible embodiments set forth in the examples but should be given the broadest interpretation consistent with the description as a whole.

What is claimed is:

1. A plethysmograph comprising:
   a housing forming a test chamber defining a test cavity configured to enclose a test subject, and a reference chamber distinct from the test chamber and defining a reference cavity;
   the test chamber comprising a test pneumotach having a test pneumotach body in which a test airflow opening is formed, for the test cavity to be in fluid communication with the outside of the housing;
   the reference chamber comprising a reference pneumotach having a reference pneumotach body in which a reference airflow opening is formed, for the reference cavity to be in fluid communication with the outside of the housing; and
   wherein, when in use, a comparison of pressure variations of air circulating in the test airflow opening and the reference airflow opening is representative of a respiratory function of the test subject;
   wherein one of the test pneumotach body and the reference pneumotach body at least partially extends in the other one of the test pneumotach body and the reference pneumotach body.

2. The plethysmograph according to claim 1, wherein at least one of the test pneumotach body and the reference pneumotach body is formed integral with the housing.

3. The plethysmograph according to claim 1, wherein said one of the test pneumotach body and the reference pneumotach body integrally extends in said other one of the test pneumotach body and the reference pneumotach body.

4. A plethysmograph comprising:
   a housing forming a test chamber defining a test cavity configured to enclose a test subject, and a reference chamber distinct from the test chamber and defining a reference cavity;
   the test chamber comprising a test pneumotach having a test pneumotach body in which a test airflow opening is formed, for the test cavity to be in fluid communication with the outside of the housing;
   the reference chamber comprising a reference pneumotach having a reference pneumotach body in which a reference airflow opening is formed, for the reference cavity to be in fluid communication with the outside of the housing; wherein
   the test pneumotach further comprises a test resistive screen at least partially covering the test airflow opening;
   the reference pneumotach further comprises a reference resistive screen at least partially covering the reference airflow opening; and wherein
   the plethysmograph further comprises a resistive plate forming the test resistive screen and the reference resistive screen.

5. The plethysmograph according to claim 1, wherein one of the test airflow opening and the reference airflow opening has a cylindrical shape and the other one of the test airflow opening and the reference airflow opening has an annular shape.

6. A plethysmograph comprising:
   a housing forming a test chamber defining a test cavity configured to enclose a test subject, and a reference chamber distinct from the test chamber and defining a reference cavity;
   the test chamber comprising a test pneumotach having a test pneumotach body in which a test airflow opening is formed, for the test cavity to be in fluid communication with the outside of the housing;
   the reference chamber comprising a reference pneumotach having a reference pneumotach body in which a reference airflow opening is formed, for the reference cavity to be in fluid communication with the outside of the housing; wherein
   one of the test airflow opening and the reference airflow opening at least partially surrounds the other one of the test airflow opening and the reference airflow opening.

7. The plethysmograph according to claim 6, wherein said one of the test airflow opening and the reference airflow opening surrounds entirely said other one of the test airflow opening and the reference airflow opening.

8. The plethysmograph according to claim 6, wherein said one of the test airflow opening and the reference airflow opening has an annular shape and the other one of the test airflow opening and the reference airflow opening has a cylindrical shape.

9. The plethysmograph according to claim 4, wherein at least one of the test pneumotach body and the reference pneumotach body is formed integral with the housing.

10. The plethysmograph according to claim 4, wherein one of the test airflow opening and the reference airflow opening has a cylindrical shape and the other one of the test airflow opening and the reference airflow opening has an annular shape.

11. The plethysmograph according to claim 4, wherein at least one of the test resistive screen and the reference resistive screen comprises at least one layer of a non-conductive substrate.

12. The plethysmograph according to claim 1, the test airflow opening defining a test airflow surface having a geometrical center, the reference airflow opening defining a reference airflow surface having a geometrical center, wherein the geometrical centers of the test airflow surface and the reference airflow surface correspond to each other.

13. The plethysmograph according to claim 4, the test airflow opening defining a test airflow surface having a geometrical center, the reference airflow opening defining a reference airflow surface having a geometrical center, wherein the geometrical centers of the test airflow surface and the reference airflow surface correspond to each other.

14. The plethysmograph according to claim 6, the test airflow opening defining a test airflow surface having a geometrical center, the reference airflow opening defining a reference airflow surface having a geometrical center, wherein the geometrical centers of the test airflow surface and the reference airflow surface correspond to each other.

15. The plethysmograph according to claim 6, wherein at least one of the test pneumotach body and the reference pneumotach body is formed integral with the housing.

* * * * *